United States Patent [19]

Macioszek et al.

[11] Patent Number: 5,698,393
[45] Date of Patent: Dec. 16, 1997

[54] METHOD FOR ELIMINATION OF RHEUMATOID FACTOR INTERFERENCE IN DIAGNOSTIC ASSAYS

[75] Inventors: Jerzy A. Macioszek; John M. Robinson, both of Gurnee, Ill.

[73] Assignee: Abbott Laboratories, Abbott Park, Ill.

[21] Appl. No.: 516,719

[22] Filed: Aug. 18, 1995

[51] Int. Cl.$^6$ .................... G01N 33/543; G01N 33/567
[52] U.S. Cl. .................... 435/5; 435/7.22; 435/7.95; 435/962; 435/967; 436/509; 436/513; 436/518
[58] Field of Search .................... 435/5, 7.22, 7.95, 435/962, 967; 436/509, 513, 518

[56] References Cited

U.S. PATENT DOCUMENTS

| | | | |
|---|---|---|---|
| 4,292,403 | 9/1981 | Duermeyer | 435/5 |
| 4,434,227 | 2/1984 | Unger | 435/7 |
| 5,073,485 | 12/1991 | Amano et al. | 435/7.94 |
| 5,556,745 | 9/1996 | Schupbach et al. | 435/5 |

FOREIGN PATENT DOCUMENTS

| | | |
|---|---|---|
| 15676 | 11/1988 | Australia. |
| 0008473 | 3/1980 | European Pat. Off.. |
| 008 473 | 3/1980 | European Pat. Off.. |
| 2 114 289 | 8/1983 | United Kingdom. |

OTHER PUBLICATIONS

Fiore, et al., "The Abbott IMx Automated Benchtop Immunochemistry Analyzer System", *Clinical Chemistry*, vol. 34, No. 9, 1 Sep. 1988, pp. 1726–1732.

AxSYM® System Toxo IgG Package Insert, Abbott Laboratories, Jun. 1995.

AxSYM® System Rubella IgG Package Insert, Abbott Laboratories, Jun. 1995.

AxSYM® System Toxo IgM Package Insert, Abbott Laboratories, Jun. 1995.

AxSYM® System Rubella IgM Package Insert, Abbott Laboratories, Jun. 1995.

Deyo, Richard A., et al., "Interference by Rheumatoid Factor with the Detection of C–Reactive Protein by the Latex Agglutination Method", *The Journal of Rheumatology* 7: 279–287, 1980.

European Society of Clinical Microbiology and Infectious Diseases, "Abstracts", 7th European Congress of Clinical Microbiology and Infectious Diseases, Mar. 26–30, 1995, Vienna, Austria, pp. 201, 202, 295.

Gispen, R., et al., "Immunofluorescence test for IgM rubella antibodies in whole serum after absorption with anti-γFc", *Clin. exp. Immunol.*, (1975) 22, 431–437.

Hagenaars, A.M., et al., "Elimination of interference of rheumatoid factor in ELISA by peptic digestion of antibodies", *Dev. Clin. Biochem.*, 1 (1980), 209–215.

Hamilton, Robert G., "Rheumatoid Factor Interference in Immunological Methods", Autoantibodies to Immunoglobulins, Shakib F (ed), Monogr. Allergy, Basel, Karger, 1989, vol. 26, pp. 27–44.

Ho, David W. T., et al., "Rapid Diagnosis of Acute Epstein–Barr Virus Infection by an Indirect Enzyme–Linked Immunosorbent Assay for Specific Immunoglobulin M (IgM) Antibody without Rheumatoid Factor and Specific IgG Interference", *Journal of Clinical Microbiology*, vol. 27, No. 5, May 1989, pp. 952–958.

IMx® System Rubella IgM Package Insert, Abbott Laboratories, Mar. 1995.

IMx® System Toxo IgM Package Insert, Abbott Laboratories, Mar. 1993.

Johnson, Roy B. Jr., et al., "Separation of Immunoglobulin M (IgM) Essentially Free of IgG from Serum for Use in Systems Requiring Assay of IgM–Type Antibodies Without Interference from Rheumatoid Factor", *Journal of Clinical Microbiology*, vol. 12, No. 3, Sep. 1980, pp. 451–454.

Kato, Kanefusa, et al., "Use of Antibody Fab' Fragments to Remove Interference by Rheumatoid Factors with the Enzyme–Linked Sandwich Immunoassay", *Febs Letters*, vol. 102, No. 2, Jun. 1979, pp. 253–256.

Kolb, G., "Rapid Adsorption of Rheumatoid Factor (RF) on Suspension of Glutaraldehyde–Crosslinked Immunoglobulin G (IGG)—Method To Avoid RF Interference", *Biomat., Art. Cells, Art. Org.*, 18(5), 605–616 (1990).

Larsson, Anders, et al., "Use of Chicken Antibodies in Enzyme Immunoassays to Avoid Interference by Rheumatoid Factors", *Clin. Chem.*, 37/3, 411–414 (1991).

Macioszek, J., et al., "Evaluation of the Abbott AxSYM Toxo IgG and IgM Antibody Assays", Abbott Laboratories, Abbott Park, IL, U.S.A.;Institut De Puericulture, Paris, France.

(List continued on next page.)

*Primary Examiner*—David Saunders
*Attorney, Agent, or Firm*—David L. Weinstein

[57] ABSTRACT

A method for treating biological samples, e.g., human sera or plasma, suspected of containing rheumatoid factors to eliminate cross-reactivity and false positive assay results in IgM immunoassays that are caused by the presence of rheumatoid factors in these biological samples. In one aspect, the method comprises diluting a biological sample with a sufficient amount of rheumatoid factor neutralization buffer to cause the pH of resulting reaction mixtures containing this sample and a solid phase material to be sufficiently low to cause rheumatoid factors in those mixtures to reduce their affinity to IgG antibodies to such an extent that they will not form a complex with IgG antibodies bound to the solid phase material, thereby facilitating the removal of these rheumatoid factors from the mixtures prior to the detection phase of a diagnostic assay. In another aspect of the invention, the method comprises introducing to a solid phase material containing a binding member-antibody complex a sufficient amount of rheumatoid factor neutralization buffer having a pH sufficiently low to cause rheumatoid factors bound to IgG antibodies bound to the solid phase material to reduce their affinity to the IgG antibodies to such an extent that the rheumatoid factors can be washed away from the solid phase material prior to the detection phase of a diagnostic assay.

31 Claims, No Drawings

OTHER PUBLICATIONS

Malyak, Mark, et al., "IL–1ra ELISA: reduction and alkylation of synovial fluid eliminates interference by IgM rheumatoid factors", *Journal of Immunological Methods*, 140 (1991) 281–288.

Meurman, O.H., et al., "IgM–class rheumatoid factor interference in the solid–phase radioimmunoassay of rubella–specific IgM antibodies", *Journal of Clincal Pathology*, 1978, 31, 483–487.

Robinson, J.M., et al., "Development of the Abbott AxSYM Rubella IgG and IgM Antibody Assays", Abbott Laboratories, Abbott Park, IL.

Salonen, Eeva–Marjatta, et al., "Rheumatoid Factor in Acute Viral Infections: Interference with Determination of IgM, IgG, and IgA Antibodies in an Enzyme Immunoassay", *The Journal of Infectious Diseases*, vol., No. 2, Aug. 1980, pp. 250–255.

Schmitz, H., et al., "Rapid Method to Detect Rubella Immunoglobulin M and Immunoglobulin A Antibodies", *Journal of Clinical Microbiology*, vol. 1, No. 2 Feb. 1976, pp. 132–135.

Vejtorp, M., "The Interference of IgM Rheumatoid Factor in Enzyme–Linked Immunosorbent Assays of Rubella IgM and IgG Antibodies", *Journal of Virological Methods*, 1 (1980), 1–9.

Weber, Theodor H., etal., "Endogenous interference in imunoassays in clinical chemistry. A rewiev.", *Scand J Clin Lab Invest* 1990; 50, Suppl 201: 77–82.

METHOD FOR ELIMINATION OF RHEUMATOID FACTOR INTERFERENCE IN DIAGNOSTIC ASSAYS

BACKGROUND OF THE INVENTION

1. Field of the Invention

This invention relates to diagnostic assays, and, more particularly, to a method for eliminating interference resulting from rheumatoid factors in biological samples.

2. Discussion of the Art

*Toxoplasma gondii* (*T. gondii*) is an obligate intracellular parasite capable of infecting a wide variety of intermediate hosts including man. Infected definitive hosts (cats) shed oocysts in feces which rapidly mature in soil and become infectious. When ingested by intermediate hosts, tachyzoites form and multiply rapidly with eventual development of cysts containing the slower growing, but infectious bradyzoites. This toxoplasmosis is acquired by man via ingestion of cat faces or undercooked meats infected with cysts.

Infection of the normal adult is commonly asymptomatic. In those cases with clinical manifestations, the most common of the symptoms is lymphadenopathy, which may be accompanied by an array of other symptoms, making differential diagnosis difficult. On the other hand, severe to fatal infections do occur in adults immunocompromised by cancer chemotherapy or immunosuppressive treatment and in patients with AIDS. Infections in the immunocompromised adults are thought to be reactivation of latent acquired infections and usually involve the central nervous system, although involvement of other sites has been reported.

Transplacental transmission of the parasite resulting in congenital toxoplasmosis can occur during the acute acquired maternal infection. The risk of fetal infection is a function of time at which acute maternal infection occurs during gestation. Maternal infections acquired before conception present very little, if any, risk to the fetus. However, the incidence of congenital toxoplasmosis increases as pregnancy progresses; conversely, the severity of congenital toxoplasmosis is greatest when maternal infection is acquired early during pregnancy. A majority of infants infected in utero are asymptomatic at birth, particularly if maternal infection occurs during the third trimester, with sequelae appearing later in life. Congenital toxoplasmosis results in severe generalized or neurologic disease in about 20-30% of the infants infected in utero; approximately 10% exhibit ocular involvement only, and the remainder (about 70%) are asymptomatic at birth. Subclinical infection may result in premature delivery and subsequent neurologic, intellectual, and audiologic defects.

Prospective studies of pregnancies have shown that prenatal diagnosis of infection followed by prenatal therapy reduces the frequency and the severity of congenital toxoplasmosis. Serologic tests can be used to identify those pregnancies at risk; women who are seronegative at the time of diagnosis of pregnancy can be monitored during pregnancy. Seroconversion is indicative of *T. gondii* infection and establishes gestational age when maternal infection occurred.

Serologic tests specific for *T. gondii* IgM antibodies are useful aids in the diagnosis of both congenital and acute acquired toxoplasmosis. Levels of IgM antibody increase rapidly following acute acquired infections and begin to decline after several months, but can persist at detectable levels for a year or more. Since persisting IgM levels may be detected long after the onset of acquired infection, the use of a single serological test result must be used with caution in those cases when it is critical to establish the time of infection. This applies to the diagnosis of acute *T. gondii* infection acquired during pregnancy. Determination of the date of infection based solely on the results of detectable IgM antibody to *T. gondii* is not recommended. That determination should include clinical history and previous serology, since low levels of IgM antibody may persist for a year or more. The use of a test to determine a rise in IgG antibody to *T. gondii* may provide additional information as to the date of infection.

Primary rubella infection in most individuals is typically a mild self-limiting disease characterized by a maculopapular rash, fever, malaise, and lymphadenopathy. In pregnant women, primary infection can have serious medical consequences. In utero infections may severely damage the fetus, particularly if occurring during the first four months of gestation. The congenitally infected infant may exhibit one or more of a variety of defects collectively known as the congenital rubella syndrome (CRS). Among these are low birth weight, cataracts, deafness, congenital heart disease, and mental retardation.

Although rubella does have typical symptomology, the clinical picture can be quite variable. The disease is often difficult or impossible to accurately diagnose from symptoms alone. With the advent of hemagglutination inhibition (HAI) testing, laboratories were able to provide serological evidence of recent rubella infection by showing increasing levels of antibody activity between paired acute and convalescent sera. However, since HAI titers increase rapidly from the date of disease onset, the acute serum must be collected early in order to detect a significant increase in titer when compared to the convalescent serum. In addition, HAI titers increase significantly following both primary infection and reinfection so HAI cannot be used to differentiate between the two. The detection of rubella IgM antibody in a single serum sample was made possible with the use of HAI testing coupled with 2-mercaptoethanol treatment or sucrose density gradient fractionation. The ability to detect the IgM class of anti-rubella antibody in a single sample overcomes some of the problems associated with paired sera analysis and provides a clearer serodiagnosis picture.

Asymptomatic reinfection of immune pregnant women, generally believed to be harmless to the fetus, is characterized serologically by a rise in IgG antibody in the absence of detectable IgM antibody. A primary infection is associated with a pronounced IgM antibody response to the rubella virus antigen. IgM antibody reactive with rubella virus antigen has been observed following reinfection; however, the levels are low and not detectable by all IgM assays. In cases of acute primary infection during pregnancy, IgM has been detected 4 to 15 days after appearance of the rash in nearly 100% of the cases. IgM levels begin to decline after 36 to 70 days, and are infrequently detected after 180 days.

Although the clinical utility of rubella IgM detection is usually associated with testing pregnancy women, testing of nonpregnant individuals for IgM antibodies to rubella virus antigen is a useful aid in diagnosis of acute infection.

Rheumatoid factors present in some sera may cause false positive results in IgM assays for *T. gondii* and rubella. To address this problem, some IgM assay protocols require that all specimens that tested positive be treated with Rheumatoid Factor Neutralization Reagents (RFNR) and retested. RFNR comprises a suspension of microparticles coated with human gamma globulin. RFNR absorbs rheumatoid factors because rheumatoid factors have an affinity for the Fc portion of the human IgG molecule. When a rheumatoid factor positive human specimen is incubated with RFNR, rheumatoid factors bind to the coated microparticles, and the bound rheumatoid factors are removed via centrifugation. The treated specimen is then retested with an alternative dilution protocol to compensate for the effect of diluting caused by the RFNR procedure. Upon retest, specimens are not interpreted as positive for the specific IgM antibodies unless those specimens remain positive following adsorption with the RFNR.

It would be desirable to eliminate the need for treatment of specimens with RFNR and retesting of specimens that were initially positive.

SUMMARY OF THE INVENTION

This invention provides a method for treating biological samples, e.g., human sera or plasma, suspected of containing rheumatoid factors to eliminate cross-reactivity and false positive assay results in IgM immunoassays that are caused by the presence of rheumatoid factors in these biological samples.

In one aspect of the invention, the method comprises introducing to a solid phase material containing a complex comprising an antibody and a binding member specific for that antibody, e.g., an antigen, a sufficient amount of rheumatoid factor neutralization buffer, which buffer has a pH sufficiently low to cause rheumatoid factors bound to IgG antibodies bound to the solid phase material to reduce their affinity to the IgG antibodies to such an extent that the bond of the rheumatoid factors to the IgG antibodies will break and the rheumatoid factors can be washed away from the solid phase material prior to the detection phase of a diagnostic assay. However, the pH of the rheumatoid factor neutralization buffer must not be so low that the binding of the IgM antibodies, e.g., anti-rubella IgM antibodies or anti-$T.\ gondii$ IgM antibodies, bound to binding members, e.g., antigens, immobilized on the solid phase material is adversely affected. In this particular aspect, the rheumatoid factor neutralization buffer will typically have a pH below about 6.5. Preferably, the rheumatoid factor neutralization buffer has a pH of from about 3.0 to about 5.5, more preferably from about 3.5 to about 5.0.

In another aspect, the method comprises introducing to a biological sample or to a reagent comprising a solid phase material having a binding member specific for IgM antibodies immobilized thereon or to both the sample and the reagent a sufficient amount of rheumatoid factor neutralization buffer, which buffer has a pH sufficiently low to cause the pH of resulting reaction mixtures containing rheumatoid factors to be sufficiently low to cause rheumatoid factors in those mixtures to reduce their affinity to IgG antibodies to such an extent that they will not form a complex with IgG antibodies bound to the solid phase material, thereby facilitating the removal of these rheumatoid factors from the mixtures prior to the detection phase of a diagnostic assay. However, the pH of the rheumatoid factor neutralization buffer must not be so low that the binding of the IgM antibodies, e.g., anti-rubella IgM antibodies or anti-$T.\ gondii$ IgM antibodies, bound to binding members, e.g., antigens, immobilized on the solid phase material will be adversely affected. In this particular aspect, the rheumatoid factor neutralization buffer will typically have a pH no higher than about 6.5. Preferably, the rheumatoid factor neutralization buffer has a pH of from about 3.0 to about 5.5, more preferably from about 3.5 to about 5.0.

In either aspect, classes of buffers that are suitable for the method of this invention include ionic, nonionic, and zwitterionic buffers preferably having a pKa value no higher than about 6.5. Representative examples of buffers that are suitable for the method of this invention include, but are not limited to, acetic acid, citric acid, formic acid, succinic acid, and glycine.

The rheumatoid factor neutralization buffer can be used to eliminate interference from rheumatoid factors in IgM immunoassays in at least one of two ways. In one way, the buffer can be used to treat complexes that are attached to the solid phase material. The buffer breaks the bonds between the rheumatoid factors and IgG antibodies that are bound to the solid phase material and elutes off the rheumatoid factors. In another way, the buffer can be added directly to a sample suspected of containing rheumatoid factors or to a reagent containing a solid phase material having immobilized thereon a binding member specific for an IgM antibody or to both the sample and the reagent. When the sample is combined with the reagent, the buffer lowers the pH of the mixture containing the sample and the reagent and interferes with the binding of rheumatoid factors with IgG antibodies in the sample that bind to the solid phase material.

The invention is particularly useful for use with automated continuous and random access analytical systems, such as that described in U.S. Pat. No. 5,358,691, incorporated herein by reference.

This invention minimizes false positive assay results that may arise from the presence of rheumatoid factors in human sera or plasma specimens. A primary benefit of this invention is its simplicity and the ability to incorporate this step into the assay protocol of an assay being run on an automated, continuous, and random access analytical system. This invention makes it possible to eliminate the requirement of treating off-line all initially positive specimens with RFNR and retesting, thereby simplifying the assay procedure and reducing the assay time required to determine the presence of IgM antibodies to $T.\ gondii$ antigen or rubella virus antigen.

DETAILED DESCRIPTION

As used herein, "test sample" or "sample" means a material suspected of containing the analyte. The test sample can be used directly as obtained from the source or following a pretreatment to modify the character of the sample. The test sample can be derived from any biological source, such as a physiological fluid, such as, for example, blood, saliva, ocular lens fluid, cerebral spinal fluid, sweat, urine, milk, ascites fluid, synovial fluid, peritoneal fluid, amniotic fluid, and the like. The test sample can be pretreated prior to use, such as preparing plasma from blood, diluting viscous fluids, and the like. Methods of treatment can involve filtration, distillation, extraction, concentration, inactivation of interfering components, the addition of reagents, and the like. Other liquid samples besides physiological fluids can be used, such as water, food products, and the like, for the performance of environmental or food production assays. In addition, a solid material suspected of containing the analyte can be used as the test sample. In some instances it may be beneficial to modify a solid test sample to form a liquid medium or to release the analyte.

As used herein, "binding member" means a member of a specific binding pair, i.e., two different molecules where one of the molecules through chemical or physical means specifically binds to the second molecule. An example of such binding members of a specific binding pair are an antigen and an antibody that specifically binds to that antigen. Another example of such binding members of a specific binding pair are a first antibody and a second antibody that specifically binds to the first antibody.

As used herein, "conjugate" means a binding member, e.g., an antigen or an antibody, coupled to a detectable moiety.

As used herein, "detectable moiety" means a moiety of a conjugate attached to a binding member, e.g., an antibody or an antigen. The detectable moiety renders the reaction between the binding member and its complementary binding member detectable. Representative examples of detectable moieties include enzymes, radioactive labels, fluorescein, and chemicals that produce light. A detectable moiety is any substance that can be attached to an analyte and that is capable of producing a signal that is detectable by visual or instrumental means. Various detectable moieties suitable for use in this invention include catalysts, enzymes, liposomes, and other vesicles containing signal producing substances such as chromogens, catalysts, fluorescent compounds, chemiluminescent compounds, enzymes, and the like. A number of enzymes suitable for use as labels are disclosed in U.S. Pat. No. 4,275,149, incorporated herein by reference. Such enzymes include glucosidases, galactosidases, phosphatases and peroxidases, such as alkaline phosphatase and horseradish peroxidase, which are used in conjunction with enzyme substrates, such as fluorescein di(galactopyranoside), nitro blue tetrazolium, 3,5',5,5'-tetranitrobenzidine, 4-methoxy-1-naphthol, 4-chloro-1-naphthol, 4-methylumbelliferyl phosphate, 5-bromo-4-chloro-3-indolyl phosphate, chemiluminescent enzyme substrates, such as the dioxetanes described in WO 88100694 and EP 0-254-051-A2, and derivatives and analogues thereof. Preferably, the detectable moiety is an enzyme and most preferably the enzyme is alkaline phosphatase.

As used herein, "solid phase material" means any material which is insoluble, or can be made insoluble by a subsequent reaction. Representative examples of solid phase materials include polymeric or glass beads, microparticles, tubes, sheets, plates, slides, wells, tapes, test tubes, or the like.

As used herein, "substrate" means a material that can be converted into a fluorescent compound, such as 4-methylumbelliferone, by an appropriate enzyme. The rate at which the fluorescent compound is formed is an indication of the quantity of enzyme present in the reaction mixture. When the enzyme is a detectable moiety, as in an enzyme immunoassay, the quantity of enzyme present is related to the quantity of analyte present in the test sample. Thus, the measurement of fluorescence can be used to determine to the quantity of analyte present in the test sample.

As used herein, "analyte" means the compound to be detected or measured. The analyte has at least one epitope or binding site.

As used herein, "rheumatoid factors" means autoantibodies directed against human IgG. Rheumatoid factors most often belong to the IgM class. They are primarily found in patients suffering from rheumatoid arthritis and may interfere in immunoassays by causing false positive results. Immunoassays particularly susceptible to interference from rheumatoid factors are indirect IgM assays in which a solid phase material coated with the specific antigen capture specific IgM antibodies. The IgM antibody-antigen complex is detected by an anti-human IgM enzyme conjugate.

As used herein, "Toxo IgM assay" means a qualitative method for the detection of *T. gondii* specific IgM antibodies in human serum and plasma (e.g., EDTA, heparin, or sodium citrate).

As used herein, "Rubella IgM assay" means a qualitative method for the detection of rubella specific IgM antibodies in human serum and plasma (e.g., EDTA, heparin, or sodium citrate). In situations where primary infection is suspected, the optimum time for specimen collection has been reported to be 1 to 2 weeks after the onset of the rash.

In order to more clearly understand the significance and operation of the present invention, it is important to be aware of the nature of the immunoassays that can be run on an apparatus of the type described in U.S. Pat. No. 5,358,691, incorporated herein by reference. Many types of immunoassays can be run on an apparatus of the type described in U.S. Pat. No. 5,358,691. In general, immunoassays can be classified into two major categories—homogeneous and heterogeneous. Homogeneous and heterogeneous immunoassays depend upon the ability of a first binding member of a binding member pair, e.g., an antigen, to specifically bind to a second binding member of a binding member pair, e.g., an antibody. A conjugate, comprising one of such binding members labeled with a detectable moiety, is employed to determine the extent of such binding. For example, such binding member pairs can be an antigen and an antibody to such antigen. The conjugate, which can comprise the antibody, either participates in a binding reaction with the antigen or does not participate in such a reaction. The amount of detectable moiety detected and measured after the reaction can be correlated to the amount of antibody present in the test sample.

Heterogeneous assays can be performed in a competitive immunoassay format or in a sandwich immunoassay format. In the competitive immunoassay format, an antigen can be immobilized to a solid phase material. The amount of detectable moiety that binds to the solid phase material can be detected, measured, and correlated to the amount of antibody present in the test sample. Examples of solid phase materials include beads, particles, microparticles, and the like.

The present invention is concerned primarily with the sandwich immunoassay format. In one example of the sandwich immunoassay format, a test sample containing an antibody is contacted with an antigen, e.g., a protein, that has been immobilized on a solid phase material, thereby forming an antigen-antibody complex. Examples of solid phase materials include beads, particles, microparticles, and the like. The solid phase material containing the antigen-antibody complex is typically treated, for example, with a second antibody that has been labeled with a detectable moiety. The second antibody then becomes bound to the antibody of the sample, which is bound to the antigen immobilized on the solid phase material. Then, after one or more washing steps to remove any unbound material, an indicator material, such as a chromogenic substance, is introduced to react with the detectable moiety to produce a detectable signal, e.g., a color change. The color change is then detected, measured, and correlated to the amount of antibody present in the test sample. It should also be noted that various diluents and buffers are also required to optimize the operation of the microparticles, antigens, conjugates, and other components of the assay that participate in chemical reactions. It should be further noted that other types of sandwich assays can be utilized, such as, for example, where the first antibody is immobilized on the solid phase material.

A heterogeneous immunoassay that can be performed with the apparatus of U.S. Pat. No. 5,358,691 in either a competitive or sandwich immunoassay format is a microparticle capture enzyme immunoassay, such as that described in *Clinical Chemistry*, Volume 34, No. 9, pages 1726–1732 (1988), employing microparticles as the solid phase material. This article is incorporated herein by reference.

A step-by-step description of a microparticle capture enzyme immunoassay procedure is set forth at col. 35, line 60 through col. 44, line 22 of U.S. Pat. No. 5,358,691.

One aspect of the method of the present invention can be conducted in the following manner. First, a biological sample is provided. Then, the sample is combined with a solid phase material having immobilized thereon a binding member specific for an antibody. An example of such a binding member is an antigen, e.g., rubella virus antigen, *T. gondii* antigen. Antibodies in the sample, if any, for which the immobilized binding member is specific, are allowed to bind to the immobilized binding member to form a binding member-antibody complex. Antibodies of particular interest in this invention include the IgM antibody to rubella virus antigen and the IgM antibody to *T. gondii* antigen. Then the solid phase material is separated from the sample, preferably by applying the mixture of solid phase material and sample to a porous matrix. The solid phase material is then washed on the matrix with a sufficient amount of a rheumatoid factor neutralization buffer, which buffer has a pH sufficiently low to cause rheumatoid factors, if present, to dissociate from IgG antibodies bound to the solid phase material. Then, it is preferred that any additional unbound materials be removed from the solid phase material by means of washing on the matrix, typically with a buffer, e.g., a neutral pH buffer. The solid phase material is then subjected to an antibody-enzyme conjugate that will bind to the binding member-antibody complex immobilized on the solid phase material. Then, unbound materials are removed from the solid phase material by means of washing on the matrix, typically with a buffer, e.g., a neutral pH buffer. A substrate for the enzyme is added to the matrix. The rate of formation of detectable product, e.g., fluorescent product, is then measured and the level of IgM antibodies in the sample is determined. It should be noted that, the expression "IgG antibodies bound to the solid phase material", as used herein, is intended to include both (1) IgG antibodies attached directly to the solid phase material and (2) IgG antibodies bound to a binding member that is attached directly to the solid phase material.

The pH of the rheumatoid factor neutralization buffer must be sufficiently low to reduce, more preferably eliminate, the binding of rheumatoid factors to the immunocomplexes consisting of IgG antibodies, e.g., anti-rubella IgG antibodies or anti-*T. gondii* IgG antibodies, bound to the solid phase material, but not so low that the binding of the IgM antibodies, e.g., anti-rubella IgM antibodies or anti-*T. gondii* IgM antibodies, bound to binding members, e.g., antigens, immobilized on the solid phase material is adversely affected. As a result of using a sufficient amount of rheumatoid factor neutralization buffer having an appropriately low pH, biological samples containing rheumatoid factors will not create false positive assay results in assays for IgM antibodies.

Another aspect of the method of the present invention can be conducted in the following manner. First, a biological sample is provided. Then a reagent comprising a solid phase material having immobilized thereon a binding member specific for an antibody of interest is provided. An example of such a binding member is an antigen, e.g., rubella virus antigen, *T. gondii* antigen. Then, the sample or the reagent or both sample and reagent is diluted in a sufficient amount of rheumatoid factor neutralization buffer, which buffer has a pH sufficiently low to prevent rheumatoid factors, if present, from binding to IgG antibodies bound to the solid phase material. Then the sample is combined with the reagent containing the solid phase material. Antibodies in the sample, if any, for which the immobilized binding member is specific, are allowed to bind to the binding member immobilized on the solid phase material to form a binding member-antibody complex. Antibodies of particular interest in this invention include the IgM antibody to rubella virus antigen and the IgM antibody to *T. gondii* antigen. Then the solid phase material is separated from the sample, preferably by applying the mixture of solid phase material and sample to a porous matrix. Then, it is preferred that any unbound materials be removed from the solid phase material by means of washing on the matrix, typically with a buffer, e.g., a neutral pH buffer. The solid phase material is then subjected to an antibody-enzyme conjugate that will bind to the binding member-antibody complex. Then, unbound materials are removed from the solid phase material by means of washing on the matrix, typically with a buffer, e.g., a neutral pH buffer. A substrate for the enzyme is added to the matrix. The rate of formation of detectable product, e.g., fluorescent product, is then measured and the level of IgM antibodies in the sample is determined. As stated previously, the expression "IgG antibodies bound to the solid phase material", as used herein, is intended to include both (1) IgG antibodies attached directly to the solid phase material and (2) IgG antibodies bound to a binding member that is attached directly to the solid phase material.

The pH of the rheumatoid factor neutralization buffer must be sufficiently low to cause the pH of resulting reaction mixtures containing rheumatoid factors to reduce, more preferably prevent, the binding of rheumatoid factors to the immunocomplexes consisting of IgG antibodies, e.g., anti-rubella IgG antibodies or anti-*T. gondii* IgG antibodies, bound to the solid phase material, but not so low that the binding of IgM antibodies, e.g., anti-rubella IgM antibodies or anti-*T. gondii* IgM antibodies, to binding members, e.g., antigens, on the solid phase material is adversely affected. As a result of using a sufficient amount of rheumatoid factor neutralization buffer having an appropriately low pH, biological samples containing rheumatoid factors will not create false positive assay results in assays for IgM antibodies.

In either aspect, classes of buffers that are suitable for the method of this invention include ionic, nonionic, and zwitterionic buffers having a pKa value no higher than about 6.5. Additional details on the meaning of pH and pKa can be found in "Buffers—A guide for the preparation and use of buffers in biological systems", Donald E. Gueffroy, editor, Calbiochem-Novabiochem (1975), incorporated herein by reference. Representative examples of buffers that are suitable for the method of this invention include, but are not limited to, acetic acid, citric acid, formic acid, succinic acid, and glycine.

Buffers that are suitable for the present invention preferably have a pH ranging from about 3.0 to about 6.5, more preferably from about 3.5 to about 5.5, most preferably from about 3.5 to about 5.0. If the pH of the rheumatoid factor neutralization buffer is too low, the binding members of interest will not bind to form complexes. If the pH of the rheumatoid factor neutralization buffer is too high, rheumatoid factors will bind to IgG antibodies bound to the solid phase material and yield false positive test results. It is also preferred that antimicrobial agents be included with the buffer.

During use, the rheumatoid factor neutralization buffer should be present in a concentration that will yield the appropriate level of pH. When the rheumatoid factor neutralization buffer is used to wash the binding member-antibody complex on a solid phase material on a porous matrix, the pH of the buffer will not vary because the buffer will not be affected by the biological sample. If the rheumatoid factors are bound to a complementary binding member, such as IgG antibodies bound to the solid phase material, subjecting the complex containing the rheumatoid factors to a rheumatoid factor neutralization buffer having the appropriate pH will cause the complexes containing rheumatoid factors to break down, thereby allowing the unbound rheumatoid factors to be washed away. However, when the rheumatoid factor neutralization buffer is used in a mixture containing the biological sample, the biological sample can cause the pH of the mixture to vary. Accordingly, in this situation, it is desirable to rely on pKa values as a means of regulating the pH of the environment for eliminating rheumatoid factors. If the rheumatoid factors in a sample are not bound to a complementary binding member, e.g., IgG antibodies bound to the solid phase material, maintaining the rheumatoid factors in an environment having the appropriate pH will prevent them from binding to a complementary binding member.

Because suitable concentrations of the rheumatoid factor neutralization buffer can vary over a wide range, it is difficult to state the precise amount of rheumatoid factor neutralization buffer needed for a given assay. In general, in the aspect wherein the solid phase material containing the binding member-antibody complex is washed, the amount of rheumatoid factor neutralization buffer required is dependent upon the surface area of the porous matrix. In the aspect wherein the sample or the reagent containing the solid phase material or both sample and reagent is diluted, the amount of rheumatoid factor neutralization buffer required is dependent upon the dynamics of the assay protocol, e.g., reagent volumes. In IgM assays, e.g., the Toxo IgM assay and in the Rubella IgM assay run on the AxSYM® instrument, suitable amounts of rheumatoid factor neutralization buffer and the pH thereof can be calculated by calibrating against known samples. Such calibration can be readily carried out by one of ordinary skill in the art.

The rheumatoid factor neutralization buffer can be introduced in the assay procedure at any of several points. For example, the buffer can be introduced at the beginning of the procedure to an untreated biological sample or to a reagent containing a solid phase material to which is bound a specific binding member, e.g., an antigen, or to both sample and reagent. It is preferred to dilute the sample only. However, it is also possible to dilute the reagent only or to dilute both the sample and the reagent. Regardless of which component of the assay is diluted by the rheumatoid factor neutralization buffer, the principle of eliminating rheumatoid factors is the same. Of course, if the reagent only is diluted, elimination of rheumatoid factors from the sample will not occur until the sample is combined with the reagent. Alternatively, the buffer can be used to wash solid phase materials containing complexes comprising binding member pairs, e.g., antigen-antibody complexes, that have formed via the reaction of binding members in the sample, e.g., antibodies, with binding members attached to the solid phase material, e.g., antigens.

In the Toxo IgM assay and in the Rubella IgM assay false positive results are often caused by the presence of rheumatoid factors in human sera or plasma. For the Toxo IgM assay, rheumatoid factor neutralization buffer preferably at a pH of from about 4.0 to about 5.0 can be applied onto the matrix after the reaction mixture consisting of microparticles coated with *T. gondii* antigen and biological sample is applied to the matrix. Rheumatoid factors bound to anti-*T. gondii* IgG antibodies captured by the microparticles are eluted.

For the Rubella IgM assay, rheumatoid factor neutralization buffer preferably at a pH of from about 4.0 to about 5.0 can be applied onto the matrix after the reaction mixture consisting of microparticles coated with rubella virus antigen and biological sample is applied to the matrix. Rheumatoid factors bound to anti-rubella IgG antibodies captured by the microparticles are eluted.

Alternatively, for either the Toxo IgM assay or the Rubella IgM assay, samples containing human sera or plasma or other biological fluids can be diluted with rheumatoid factor neutralization buffer prior to mixing the sample with the microparticles coated with the antigen of interest.

Turning now to details of the microparticle capture enzyme immunoassay typically used in the Toxo IgM assay and in the Rubella IgM assay, the presence of IgM antibodies is measured by using a solid phase material having a binding member specific for IgM antibody of interest bound thereto. An example of a solid phase material is a microparticle coated with an antigen capable of binding with the specific antibody of interest. The sample is combined with the solid phase material to form a mixture; the mixture is incubated, whereby the antigen combines with the antibody of interest. The solid phase material and the test sample are separated so that the amount of IgM antibody bound to the antigen-coated solid phase material can be determined. The amount of IgM antibody bound to the solid phase material is preferably determined by enzyme immunoassay, wherein an anti-human IgM antibody labelled with an enzyme is used as the conjugate. A material referred to as an enzyme substrate can be converted into a fluorescent compound, such as 4-methylumbelliferone, by an appropriate enzyme. The rate at which the fluorescent compound is formed is an indication of the quantity of enzyme present in the reaction mixture. When the enzyme is the detectable moiety, as in an enzyme immunoassay, the quantity of enzyme present is related to the quantity of conjugate present in the test sample. Thus, the measurement of fluorescence can be used to determine to the quantity of IgM antibody present in the test sample. The amount of anti-human IgM conjugate on the solid phase material can be correlated to the concentration of IgM antibody in the test sample by means of a plot showing enzyme activity as a function of concentration of IgM antibody, typically referred to as a standard curve. A standard curve can be prepared by performing the assay using calibrators, which are known to one having ordinary skill in the art. Alternatively, particularly in the case of assays for IgM antibodies, a single index calibrator is used to determine cutoff values for the assay. Controls are used to verify that the calibration is valid. When a sample having an unknown level of IgM antibody is assayed, the measured assay signal is compared to the index calibrator, and the index value level corresponding to the measured signal is the level of IgM antibody in the sample.

A specific binding member may be bound to the solid phase by physical or chemical means, preferably by means of a covalent bond or by hydrophobic interaction. The specific binding member should be bound to the solid phase in such a way that substantially none of the specific binding members detach during the subsequent reactions and wash steps. Regardless of the specific binding member and the coupling method selected, the specific binding member must be able to bind to the IgM antibodies in the sample after being coupled to the solid phase material.

A solid phase material according to the present invention may be a mixture of microparticles with binding members specific for the analyte of interest chemically or physically bound to the microparticles. Microparticles that can be used in this invention are preferably made of polymeric material, and more preferably include microparticles derived from polymers having styrene units or polymers having acrylate units. The microparticles are preferably substantially spherical and preferably have radii ranging from about 0.1 μm to about 0.25 inches. A preferred method for separating these particles from the test sample involves capture of the microparticle on a porous matrix, such as a glass fiber.

A porous matrix suitable for use in this invention can be any suitable porous material. As used herein, "porous material" means a material through which fluids can flow and can easily pass. Representative examples of materials suitable for the porous matrix include, but are not limited to, olefin polymers, e.g., polypropylene, polyethylene, fluorinated olefin polymers, e.g., polytetrafluorethylene, fiberglass, cellulose, or nylon.

Preferred materials for the porous matrix include a porous fiberglass material, such as a "Whatman 934-AH" filter paper, which has a nominal thickness of 0.33 mm, or the disposable IMx® cartridge and TestPack™ (fiber matrix) devices (Abbott Laboratories, Abbott Park, Ill. 60064). The thickness of such material is not critical, and will be a matter of choice, based upon the properties of the test sample or analyte being assayed, such as the fluidity of the test sample. In addition, preferred materials are commercially available in matrix cells from Abbott Laboratories, Abbott Park, Ill. 60064 under catalog numbers 4B25-20 (AxSYM® Toxo IgM Reagent Pack) and 4B46-20 (AxSYM® Rubella IgM Reagent Pack).

As stated previously, an enzyme substrate can be converted into a fluorescent compound, such as 4-methylumbelliferone, by an appropriate enzyme. The rate at which the fluorescent compound is formed is an indication of the quantity of enzyme present in the reaction mixture. When the enzyme is the detectable material, the quantity of enzyme present is related to the quantity of IgM antibodies present in the test sample. Thus, the measurement of fluorescence resulting from enzyme activity in an enzyme immunoassay can be used to determine the quantity of IgM antibodies present in the test sample. Fluorescence can be measured by any method known to the art. For example, a fluorescence spectrometer can be used. The fluorescence spectrum can also be observed by means of a visual spectrometer or by a photograph with a spectrograph of high light-gathering power.

The following examples are illustrative of the invention and are not to be interpreted as limiting the scope of the invention, as defined in the claims.

EXAMPLE 1

Toxoplasmosis gondii IgM Assay

AxSYM® Assay Format

The *Toxoplasmosis gondii* IgM assay was performed on the AxSYM® instrument, i.e., the instrument described in U.S. Pat. No. 5,358,691, according to the following procedure. Serum or plasma samples and all reagents required for one test were pipetted by the sampling probe (see first transfer pipette mechanism 6 of U.S. Pat. No. 5,358,691) into the appropriate wells of a reaction vessel in the sampling center (see front end carousel 4, sample cup carousel 28, reaction vessel carousel 36, and reagent pack carousel 32 of U.S. Pat. No. 5,358,691). The reaction vessel was immediately transferred into the process center (see process carousel 46 of U.S. Pat. No. 5,358,691). Further pipetting was carried out in the processing center at the processing probe (see second transfer pipette mechanism 50 of U.S. Pat. No. 5,358,691).

Initially, serum or plasma (10 μL) was diluted at a 1:27 ratio with AxSYM® Line Diluent (0.1M phosphate buffer, pH 7.5) by the sampling probe. An aliquot containing diluted sample and AxSYM® *T. gondii* Coated Microparticles (strain RH) was delivered to an incubation well of the reaction vessel to form a reaction mixture. The diluted sample was drawn from a dilution well and the coated microparticles were drawn from a reagent pack. The reaction mixture was incubated for approximately eight (8) minutes at a temperature of 35° C.

AxSYM® Assay Diluent (0.05M Tris, 25% calf serum, pH 7.5) was added to the reaction mixture and an aliquot of the microparticles containing the antigen-antibody complex was transferred to the matrix cell of the AxSYM® instrument. The microparticles bound irreversibly to the glass fiber matrix of the matrix cell. The matrix cell was washed with rheumatoid factor neutralization buffer (RF Neutralization Buffer, 100 μL, 0.1M citrate, pH 4.8) to remove rheumatoid factor interference antibodies, if any, from the microparticles containing the antigen-antibody complex. The matrix cell was washed to remove unbound materials.

Goat anti-human IgM antibody:alkaline phosphatase conjugate (25 μL at a concentration of 1 μg/mL in conjugate buffer (0.5M Tris, 5% mouse serum, pH 7.2)) was dispensed onto the matrix cell and the resultant combination was incubated for approximately eight (8) minutes at a temperature of 35° C. The matrix cell was washed to remove unbound materials.

A solution of the substrate, 4-methylumbelliferyl phosphate (MUP) in aminomethyl phosphate buffer (1.2 mM), was added to the matrix cell, and the rate of formation of 4-methylumbelliferone was measured by fluorescence reflectance. Fluorescent product, 4-methylumbelliferone, was measured by the microparticle enzyme immunoassay (MEIA) optical assembly of the AxSYM® instrument.

The AxSYM® system calculated an Index Value for the Toxo IgM assay based on the ratio of the Sample Rate to the Index Calibrator Mean Rate for each sample and control.

Index Value=Sample Rate/Index Calibrator Mean Rate

The aforementioned rates are based on rate of formation of fluorescent product, typically measured in counts per second per second. Samples having an Index Value lower than 0.500 were considered to be negative for IgM antibodies to *T. gondii* by the criteria of the AxSYM® Toxo IgM assay. Samples having an Index Value of from 0.500 to 0.599 were considered equivocal. Samples interpreted as equivocal may contain very low levels of IgM. Samples having an Index Value equal to or greater than 0.600 were considered to be positive for IgM antibodies to *T. gondii* antigen by the criteria of the AxSYM® Toxo IgM assay.

Materials needed for the assay, including AxSYM® RF Neutralization Buffer (citrate containing antimicrobial agents), AxSYM® *T. gondii* Coated Microparticles (in buffer with protein stabilizers and containing antimicrobial agents), anti-human IgM antibody:alkaline phosphatase conjugate (in buffer with protein stabilizers and containing 0.2% sodium azide), AxSYM® Assay Diluent (buffer with protein stabilizers and containing antimicrobial agents), 4-methylumbelliferyl phosphate substrate (1.2 mM, in buffer, and containing 0.1% sodium azide), AxSYM® Line Diluent (0.1M phosphate buffer and containing antimicrobial agents), AxSYM® instruments and commodities were available commercially from Abbott Laboratories, Abbott Park, Ill. (catalog no. 4B25-20).

IMx® Assay Format

The *Toxo gondii* IgM assay was performed on the IMx® instrument according to the manufacturer's instructions (catalog no. 7A82-20). The purpose for using this format is to show that the assay of the present invention performs equal to or better than a well-known assay in the art.

This analyzer contains an optical assembly comprising a fluorometer that uses a mercury arc lamp as its light source. This instrument is described by Fiore et al (Clin. Chem., 34/9:1726–1732, 1988), incorporated herein by reference. The instrument utilizes IMx® disposable cartridges (commercially available from Abbott Laboratories, Abbott Park, Ill.), which contain a porous matrix to capture microparticles containing complexes resulting from the reaction of antigens with antibodies from the sample. The bound IgM antibodies are then detected with the goat anti-human IgM:enzyme conjugate. The label used in the conjugate is preferably alkaline phosphatase. The microparticles are separated from the reaction mixture, conjugate is added to the microparticles, conjugate binds to available IgM antibodies, and the quantity of conjugate present on the microparticles is determined from the rate at which 4-methylumbelliferyl phosphate is converted into 4-methylumbelliferone. The quantity of IgM antibodies in the sample can be determined from a standard curve of rate of 4-methylumbelliferone formation as a function of IgM antibody concentration.

The index calibrator that relates the rate of formation of 4-methylumbelliferone to IgM antibody concentration is similar to that described for the AxSYM® Toxo IgM assay. One of ordinary skill in the art would be capable of devising calibrator and control formulations suitable for the IMx® Toxo IgM assay.

In brief, a serum or plasma sample was diluted at a 1:30 ratio with IMx® MEIA buffer (0.5M Tris, pH 7.5) and mixed with *T. gondii* Coated Microparticles. The reaction mixture was incubated for approximately eight (8) minutes at a temperature of 35° C.

An aliquot of the microparticles containing the antigen-antibody complex was transferred to the matrix cell of the IMx® instrument. The microparticles bound irreversibly to the glass fiber matrix of the matrix cell. The matrix cell was washed to remove unbound materials.

Goat anti-human IgM antibody:alkaline phosphatase conjugate (25 µL at a concentration of 1 µg/mL in conjugate buffer (0.5M Tris, 5% mouse serum, pH 7.2)) was dispensed onto the matrix cell and the resultant combination was incubated for approximately eight (8) minutes at a temperature of 35° C. The matrix cell was washed to remove unbound materials.

A solution of the substrate, 4-methylumbelliferyl phosphate (MUP) in aminomethyl phosphate buffer (1.2 mM), was added to the matrix cell, and the rate of formation of 4-methylumbelliferone was measured by fluorescence reflectance. Fluorescent product, 4-methylumbelliferone, was measured by the microparticle enzyme immunoassay (MEIA) optical assembly of the IMx® instrument.

The IMx® System calculated an Index Value for the Toxo IgM assay based on the ratio of the Sample Rate to the Index Calibrator Mean Rate for each sample and control.

Index Value=Sample Rate/Index Calibrator Mean Rate

The aforementioned rates are based on rate of formation of fluorescent product, typically measured in counts per second per second. Samples having an Index Value less than 0.500 were considered to be negative for IgM antibodies to *T. gondii* antigen by the criteria of IMx® Toxo IgM assay. Samples having an Index Value ranging from 0.500 to 0.599 were considered equivocal. Samples interpreted as equivocal may contain very low level of IgM. Samples having an Index Value equal to or greater than 0.600 were considered to be positive for IgM antibodies to *T. gondii* antigen by the criteria of IMx® Toxo IgM assay.

All positive and equivocal specimens, i.e., those having an Index Value greater than 0.500, were treated with the IMx® Rheumatoid Factor Neutralization Reagent (human IgG coated microparticles; catalog no. 1A14-22) and retested.

Results

1. Buffer pH Optimization

Three lots of citrate buffer at pH values ranging from pH 4.0 to pH 5.6 and three lots of phosphate buffer at pH 7.5 were prepared and evaluated against four samples using the AxSYM® Toxo IgM assay previously described. The IMx® Toxo IgM Negative Control (NC) and the IMx® Toxo IgM Positive Control (PC) were obtained from Abbott Laboratories, Abbott Park, Ill. (catalog no. 7A82-10). The RF 1, RF 2, RF 3, and RF 4 samples were prepared samples containing rheumatoid factors and *T. gondii* IgG antibody. These samples were initially determined to be positive by the IMx® Toxo IgM assay and then negative following treatment with IMx® Rheumatoid Factor Neutralization Reagent. The results of the tests using the rheumatoid factor neutralization buffer with the AxSYM® instrument are set forth in Table I.

TABLE I

| Sample | pH 4.0 | pH 4.2 | pH 4.5 | pH 5.0 | pH 5.2 | pH 5.6 | pH 7.5 |
|---|---|---|---|---|---|---|---|
| Lot 1 | | | | | | | |
| NC | 0.134 | 0.143 | 0.111 | 0.105 | 0.114 | 0.11 | 0.113 |
| PC | 1.571 | 1.819 | 1.663 | 1.546 | 1.646 | 1.738 | 1.662 |
| RF 1 | 0.253 | 0.281 | 0.250 | 0.252 | 0.305 | 0.353 | 0.908 |
| RF 2 | 0.393 | 0.409 | 0.385 | 0.452 | 0.553 | 0.935 | 3.539 |
| RF 3 | 0.333 | 0.348 | 0.380 | 0.455 | 0.567 | — | 4.189 |
| RF 4 | 0.318 | 0.351 | 0.297 | 0.464 | 0.414 | 0.581 | 1.717 |
| Lot 2 | | | | | | | |
| NC | 0.159 | 0.160 | 0.131 | 0.125 | 0.119 | 0.137 | 0.131 |
| PC | 1.602 | 1.772 | 1.716 | 1.702 | 1.611 | 1.608 | 1.700 |
| RF 1 | 0.325 | 0.404 | 0.281 | 0.302 | 0.301 | 0.418 | 1.337 |
| RF 2 | 0.465 | 0.599 | 0.455 | 0.528 | 0.643 | 1.347 | 4.548 |
| RF 3 | 0.423 | 0.537 | 0.437 | 0.575 | 0.704 | 2.221 | 5.653 |
| RF 4 | 0.406 | 0.517 | 0.339 | 0.550 | 0.489 | 0.879 | 5.595 |
| Lot 3 | | | | | | | |
| NC | 0.173 | 0.142 | 0.134 | 0.136 | 0.142 | 0.133 | 0.154 |
| PC | 1.837 | 1.712 | 1.518 | 1.763 | 1.725 | 1.608 | 1.752 |
| RF 1 | 0.309 | 0.285 | 0.254 | 0.277 | 0.22 | 0.366 | 1.238 |
| RF 2 | 0.482 | 0.436 | 0.424 | 0.508 | 0.58 | 1.078 | 3.693 |
| RF 3 | 0.446 | 0.395 | 0.366 | 0.454 | 0.548 | 1.296 | 4.937 |
| RF 4 | 0.398 | 0.387 | 0.292 | 0.493 | 0.409 | 0.640 | 2.502 |

The data in Table I demonstrate that with an index cut-off for positive samples of 0.600, the pH range for the citrate buffer that was most effective in preventing rheumatoid factor interference was pH 4.0 to pH 5.0. The only sample that was positive for IgM antibodies to *T. gondii* antigen was the PC sample. The four rheumatoid factor positive samples (RF 1, RF 2, RF 3, and RF 4) were correctly identified as negative for IgM antibodies to *T. gondii* antigen when the pH of the buffer was no higher than pH 5.0.

2. Sample Evaluation

A. Clinical Rheumatoid Factor Samples.

Five rheumatoid factor clinical specimens were evaluated on the IMx® Toxo IgM assay format with and without treatment by IMx® Rheumatoid Factor Neutralization Reagent (catalog no. 1A14-22). In addition, the samples were evaluated by the AxSYM® Toxo IgM assay. Table II shows the Index Values obtained for the sample set.

TABLE II

| Sample Number | Untreated IMx ® Index | Treated IMx ® Index | AxSYM ® Index |
| --- | --- | --- | --- |
| 1 | 0.627 | 0.212 | 0.238 |
| 2 | 1.006 | 0.333 | 0.224 |
| 3 | 0.553 | 0.220 | 0.135 |
| 4 | 0.538 | 0.370 | 0.396 |
| 5 | 0.503 | 0.368 | 0.272 |

The results of this experiment demonstrated that the AxSYM® Toxo IgM assay utilizing the low pH rheumatoid factor neutralization buffer on-line yielded similar results to the IMx® Toxo IgM assay that employed treatment with IMx® Rheumatoid Factor Neutralization Reagent off-line.

B. Prepared Rheumatoid Factor Samples.

Nine samples containing rheumatoid factors were prepared by mixing *T. gondii* IgG antibody positive specimens with rheumatoid factor positive specimens to create false positive specimens for the IMx® Toxo IgM assay. In addition, the rheumatoid factor neutralization buffer (pH 4.5) that was used in the AxSYM® Toxo IgM assay was substituted with the MEIA buffer (pH 7.5) that was used in the IMx® Toxo IgM assay. These samples were evaluated and the results are shown in Table III.

TABLE III

| Sample Number | AxSYM ® Assay (pH 4.5) Index | AxSYM ® Assay (pH 7.5) Index |
| --- | --- | --- |
| 1 | 0.361 | 0.493 |
| 2 | 0.354 | 0.969 |
| 3 | 0.332 | 0.419 |
| 4 | 0.297 | 0.481 |
| 5 | 0.470 | 3.364 |
| 6 | 0.389 | 2.349 |
| 7 | 0.461 | 0.411 |
| 8 | 0.418 | 3.082 |
| 9 | 0.345 | 0.734 |

The results of this experiment demonstrated that the wash with pH 4.5 buffer eluted the rheumatoid factors, but the wash with pH 7.5 buffer did not elute the rheumatoid factors. Thus, the low pH rheumatoid factor neutralization buffer helped to minimize the number of false positive test results.

EXAMPLE 2

Rubella IgM Assay

AxSYM® Assay Format

The Rubella IgM assay was performed on the AxSYM® instrument according to the following procedure. Serum or plasma samples and all reagents required for one test were pipetted by the sampling probe (see first transfer pipette mechanism 6 of U.S. Pat. No. 5,358,691) into the appropriate wells of a reaction vessel in the sampling center (see front end carousel 4, sample cup carousel 28, reaction vessel carousel 36, and reagent pack carousel 32 of U.S. Pat. No. 5,358,691). The reaction vessel was immediately transferred into the process center (see process carousel 46 of U.S. Pat. No. 5,358,691). Further pipetting was carried out in the processing center at the processing probe (see second transfer pipette mechanism 50 of U.S. Pat. No. 5,358,691).

Serum or plasma was diluted at a 1:30 ratio in rheumatoid factor neutralization buffer (AxSYM® RF Neutralization Buffer, 0.5M citrate, pH 4.5) by the sampling probe. An aliquot of diluted sample and AxSYM® Rubella Virus Coated Microparticles (strain HPV 77) was delivered to an incubation well of the reaction vessel to form a reaction mixture. The diluted sample was drawn from a dilution well and the coated microparticles were drawn from a reagent pack. The reaction mixture was incubated for approximately eight (8) minutes at a temperature of 35° C.

AxSYM® Assay Diluent (0.5M Tris, 25% calf serum, pH 7.5) was added to the reaction mixture and an aliquot of the microparticles containing antigen-antibody complex was transferred to the matrix cell of the AxSYM® instrument. The microparticles bound irreversibly to the glass fiber matrix of the matrix cell. The matrix cell was washed with AxSYM® Line Diluent (0.1M phosphate buffer, pH 7.2) to remove unbound materials.

Goat anti-human IgM antibody:alkaline phosphatase conjugate (25 µL at a concentration of 1 µg/mL in conjugate buffer (0.5M Tris, 5% fetal calf serum, pH 7.2)) was dispensed onto the matrix cell and incubated for approximately eight (8) minutes at a temperature of 35° C. The matrix cell was washed to remove unbound materials.

A solution of the substrate, 4-methylumbelliferyl phosphate in aminomethyl phosphate buffer (1.2 mM, 50 µL), was added to the matrix cell, and the rate of formation of 4-methylumbelliferone was measured by fluorescence reflectance. Fluorescent product, 4-methylumbelliferone, was measured by the MEIA optical assembly.

The AxSYM® System calculated a Rubella IgM Index Value based on the ratio of the sample rate to the Index Calibrator Mean Rate for each sample and control.

Index Value=Sample Rate/Index Calibrator Mean Rate

The aforementioned rates are based on rate of formation of fluorescent product, typically measured in counts per second per second. Samples having an Index Value less than 0.600 were considered to be negative for IgM antibodies to rubella virus antigen by the criteria of AxSYM® Rubella IgM assay. Samples having an Index Value of from 0.600 to 0.799 were considered equivocal. Samples interpreted as equivocal may contain very low levels of Rubella IgM. Samples having an Index Value equal to or greater than 0.800 were considered to be positive for IgM antibodies to rubella virus antigen by the criteria of AxSYM® Rubella IgM assay and may be indicative of primary rubella infection.

Materials needed for the assay, including AxSYM® RF Neutralization Buffer (citrate and containing antimicrobial agents), AxSYM® Assay Diluent (buffer with protein stabilizers and containing antimicrobial agents), AxSYM® Rubella Virus Coated Microparticles (in buffer with protein stabilizers and containing antimicrobial agents), Anti-Human IgM (goat):Alkaline Phosphatase Conjugate (in buffer with protein stabilizers and containing 0.1% sodium azide), 4-methylumbelliferyl phosphate substrate (1.2 mM, in buffer and containing 0.1% sodium azide), AxSYM® Line Diluent (0.1M phosphate buffer and containing antimicrobial agents), AxSYM® instruments and commodities are available commercially from Abbott Laboratories, Abbott Park, Ill. (Catalog No. 4B46-20).

IMx® Assay Format

The Rubella Virus IgM assay was performed on the IMx® instrument according to the manufacturer's instructions (Catalog No. 7A24-20). Operation of the instrument was described previously in Example 1. The purpose for using this format is to show that the assay of the present invention performs equal to or better than a well-known assay in the art.

In brief, a serum or plasma sample was diluted at a 1:10 ratio with IMx® MEIA assay buffer (0.5M Tris, pH 7.5) and mixed with the AxSYM® Rubella Virus Coated Microparticles (strain HPV 77) to form a reaction mixture. The reaction mixture was incubated for approximately eight (8) minutes at a temperature of 35° C.

An aliquot of the microparticles containing the antigen-antibody complex was transferred to the matrix cell of the IMx® instrument. The microparticles bound irreversibly to the glass fiber matrix of the matrix cell. The matrix cell was washed to remove unbound materials.

Goat anti-human IgM antibody:alkaline phosphatase conjugate (25 μL at a concentration of 1 μg/mL in conjugate buffer (0.5M Tris, 25% fetal calf serum, pH 7.2)) was dispensed onto the matrix cell and the resultant combination was incubated for approximately eight (8) minutes at a temperature of 35° C. The matrix cell was washed to remove unbound materials.

A solution of the substrate, 4-methylumbelliferyl phosphate (MUP) in aminomethyl phosphate buffer (1.2 mM), was added to the matrix cell, and the rate of formation of 4-methylumbelliferone was measured by fluorescence reflectance. Fluorescent product, 4-methylumbelliferone, was measured by the microparticle enzyme immunoassay (MEIA) optical assembly of the IMx® instrument.

The IMx® System calculated a Rubella Virus Index Value based on the ratio of the sample rate to the Index Calibrator Mean Rate for each sample and control.

Index Value=Sample Rate/Index Calibrator Mean Rate

The aforementioned rates are based on rate of formation of fluorescent product, typically measured in counts per second per second. Samples having an Index Value less than 0.800 were considered to be negative for IgM antibodies to rubella virus antigen by the criteria of IMx® Rubella IgM assay. Samples having an Index Value of 0.800 to 0.999 were considered to be equivocal. Samples interpreted as equivocal might contain very low level of Rubella IgM antibodies. Samples having an Index Value equal to or greater than 1.000 were considered to be positive for IgM antibodies to rubella virus antigen by the criteria of IMx® Rubella IgM assay and might be indicative of primary rubella infection.

All positive and equivocal samples, i.e., those having an Index Value greater than or equal to 0.800, were treated with the IMx® Rheumatoid Factor Neutralization Reagent (human IgG coated microparticles; catalog no. 1A14-22) and retested.

Results

1. Buffer pH Optimization

Citrate buffers at pH values varying from pH 3.5 to pH 5.5 and phosphate buffer at pH 7.5 were prepared and evaluated using five samples using the AxSYM® Rubella IgM assay previously described. The IMx® Rubella IgM Positive Control (PC) and the IMx® Rubella IgM Negative Control (NC) samples were obtained from Abbott Laboratories, Abbott Park, Ill. (catalog no. 7A24-10). The, RF P4, RF FY3 and RF FY4 samples were clinical specimens containing rheumatoid factors and Rubella IgG antibody. These samples were initially determined to be positive by the IMx® Rubella IgM assay and then negative following treatment with IMx® Rheumatoid Factor Neutralization Reagent. The results of the tests using the rheumatoid factor neutralization buffer with the AxSYM® instrument are set forth in Table IV.

TABLE IV

| Sample | pH 3.5 | pH 4.0 | pH 4.5 | pH 5.0 | pH 5.5 | pH 7.5 |
|--------|--------|--------|--------|--------|--------|--------|
| IgM Positive | 0.99 | 1.38 | 1.57 | 1.54 | 1.45 | 1.59 |
| IgM Negative | 0.10 | 0.09 | 0.09 | 0.08 | 0.15 | 0.17 |
| RF P4 | 0.27 | 0.31 | 0.24 | 0.29 | 0.64 | 1.32 |
| RF FY3 | 0.44 | 0.47 | 0.48 | 0.46 | 0.89 | 1.09 |
| RF FY4 | 0.27 | 0.29 | 0.29 | 0.48 | 1.25 | 2.53 |

The data in Table IV demonstrate that with an index cut-off for positive samples of 0.600, the pH range for the citrate buffer that was most effective in preventing rheumatoid factor interference was pH 3.5 to pH 5.0. The only sample that was positive for IgM antibodies to rubella virus antigen was the IgM Positive Sample. The three rheumatoid factor positive samples (RF P4, RF FY3, and RF FY4) were correctly identified as negative for IgM antibodies to rubella virus antigen when the pH of the buffer was no higher than pH 5.0.

2. Sample Evaluation

A. Clinical Rheumatoid Factor Samples.

One hundred fifty seven (157) rheumatoid factor positive clinical samples were evaluated on the IMx® assay format and the AxSYM® Rubella IgM assay format. In addition, the rheumatoid factor neutralization buffer (pH 4.5) used in the AxSYM® Rubella IgM assay was substituted with the MEIA buffer (pH 7.5) used in the IMx® Rubella IgM assay. Thirty six (36) samples were rheumatoid factor positive or equivocal and were retested on the IMx® Rubella IgM assay after treatment with IMx® Rheumatoid Factor Neutralization Reagent (human IgG coated microparticles; catalog no. 1A14-22). In order to demonstrate the efficacy of the low pH AxSYM® Rubella IgM assay format, the 36 samples were also evaluated on the AxSYM® Rubella IgM assay format using the MEIA buffer (pH 7.5) for diluting the sample. Table V shows the Index Values obtained for the set of samples.

TABLE V

| Sample Number | IMx® Rubella IgM assay (pH 7.5) | IMx® Rubella IgM assay (following rheumatoid factor neutralization) | AxSYM® Rubella IgM assay (pH 4.5) | AxSYM® Rubella IgM assay (pH 7.5) |
|---|---|---|---|---|
| 88 | 0.86 | 0.15 | 0.18 | 0.89 |
| 101 | 1.31 | 0.17 | 0.20 | 0.22 |
| 108 | 0.82 | 0.19 | 0.35 | 0.59 |
| 111 | 1.3 | 0.12 | 0.17 | 0.77 |
| 81 | 1.79 | 1.58 | 1.84 | 2.34 |
| 79 | 2.85 | 0.53 | 0.80 | 1.64 |
| 129 | 2.12 | 0.31 | 0.49 | 0.32 |

TABLE V-continued

| Sample Number | IMx® Rubella IgM assay (pH 7.5) | IMx® Rubella IgM assay (following rheumatoid factor neutralization) | AxSYM® Rubella IgM assay (pH 4.5) | AxSYM® Rubella IgM assay (pH 7.5) |
|---|---|---|---|---|
| 127 | 1.69 | 0.86 | 1.17 | 0.63 |
| 126 | 4.69 | 0.81 | 0.85 | na |
| 118 | 4.13 | 1.59 | 0.85 | 2.68 |
| 55 | 0.89 | 0.35 | 0.51 | 0.30 |
| 594 | 1.34 | 0.13 | 0.14 | 0.68 |
| 595 | 0.82 | 0.10 | 0.74 | 0.81 |
| 597 | 1.84 | 0.29 | 0.41 | 2.17 |
| 910 | 4.24 | 0.60 | 0.69 | 4.69 |
| 911 | 1.09 | 0.10 | 0.12 | 0.90 |
| 914 | 4.83 | 1.81 | 1.04 | 6.32 |
| 452 | 5.77 | 0.99 | 2.49 | 7.32 |
| 457 | 3.73 | 0.25 | 0.65 | 3.09 |
| 511 | 1.24 | 0.20 | 0.10 | 2.32 |
| 513 | 0.93 | 0.77 | 0.49 | 1.28 |
| 514 | 1.73 | 0.25 | 0.11 | 1.84 |
| 933 | 1.25 | 0.23 | 0.34 | 1.07 |
| 939 | 1.77 | 0.49 | 0.40 | 2.55 |
| 934 | 2.49 | 0.13 | 0.27 | 2.60 |
| 4 | 1.41 | 0.17 | 0.18 | 0.74 |
| 12 | 4.51 | 0.65 | 0.68 | 5.78 |
| 24 | 1.34 | 0.47 | 0.57 | 1.07 |
| 27 | 1.35 | 0.13 | 0.19 | 0.94 |
| 28 | 1.66 | 0.33 | 0.40 | 0.86 |
| 30 | 2.48 | 0.39 | 0.55 | 1.85 |
| 37 | 1.99 | 0.13 | 0.47 | 1.41 |
| 38 | 4.69 | 0.35 | 1.15 | 7.23 |
| 39 | 1.08 | 0.22 | 0.28 | 0.89 |
| 40 | 0.99 | 0.17 | 0.19 | 0.47 |
| 41 | 4.41 | 0.75 | 0.79 | 4.15 |

The results of this evaluation demonstrated that diluting the samples in rheumatoid factor neutralization buffer having pH of 4.5 eliminated the false positive reaction that would be expected with samples containing rheumatoid factors. Use of the MEIA buffer in the AxSYM® Rubella IgM assay yielded results similar to those obtained with the IMx® Rubella IgM assay that did not utilize rheumatoid factor neutralization with IMx® Rheumatoid Factor Neutralization Reagent (human IgG coated microparticles; catalog no. 1A14-22).

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for eliminating interference in a diagnostic assay for IgM antibodies, said interference resulting from the presence of rheumatoid factors, said method comprising the steps of:
   (a) providing a biological sample;
   (b) providing a reagent comprising a solid phase material having immobilized thereon a binding member specific for said IgM antibodies;
   (c) combining said biological sample and said reagent under conditions whereby said binding member immobilized on said solid phase material will react with said IgM antibodies to form a binding member-IgM antibody complex; and
   (d) introducing a sufficient amount of rheumatoid factor neutralization buffer to said solid phase material to cause said rheumatoid factors to dissociate from IgG antibodies bound to said solid phase material.

2. The method of claim 1, wherein said rheumatoid factor neutralization buffer has a PKa value no higher than about 6.5.

3. The method of claim 1, wherein said rheumatoid factor neutralization buffer is selected from the group consisting of ionic and zwitterionic buffers.

4. The method of claim 1, wherein said rheumatoid factor neutralization buffer has a pH no higher than about 6.5.

5. The method of claim 1, wherein said rheumatoid factor neutralization buffer has a pH ranging from about 3.0 to about 5.5.

6. The method of claim 1, wherein said binding member immobilized on said solid phase is rubella virus antigen.

7. The method of claim 1, wherein said binding member immobilized on said solid phase is Toxoplasmosis gondii antigen.

8. The method of claim 1, wherein said rheumatoid factor neutralization buffer is used to wash said solid phase material after said biological sample has reacted with said reagent.

9. A method for eliminating interference in a diagnostic assay for IgM antibodies, said interference resulting from the presence of rheumatoid factors, said method comprising the steps of:
   (a) providing a biological sample;
   (b) providing a reagent comprising a solid phase material having immobilized thereon a binding member specific for said IgM antibodies; and
   (c) introducing to said sample of (a) or to said reagent of (b) or to both said sample of (a) and said reagent of (b) a sufficient amount of a rheumatoid factor neutralization buffer to prevent binding of said rheumatoid factors to IgG antibodies bound to said solid phase material.

10. The method of claim 9, wherein said rheumatoid factor neutralization buffer has a PKa value no higher than about 6.5.

11. The method of claim 9, wherein said rheumatoid factor neutralization buffer is selected from the group consisting of ionic and zwitterionic buffers.

12. The method of claim 9, wherein said rheumatoid factor neutralization buffer has a pH no higher than about 6.5.

13. The method of claim 9, wherein said rheumatoid factor neutralization buffer has a pH ranging from about 3.0 to about 5.5.

14. The method of claim 9, wherein said binding member immobilized on said solid phase material is rubella virus antigen.

15. The method of claim 9, wherein said binding member immobilized on said solid phase material is Toxoplasmosis gondii antigen.

16. The method of claim 9, wherein said rheumatoid factor neutralization buffer is used to dilute said biological sample before said biological sample is contacted with said reagent.

17. The method of claim 9, wherein said rheumatoid factor neutralization buffer is used to dilute said reagent before said reagent is contacted with said biological sample.

18. A method for measuring the amount of IgM antibodies in an assay of a biological sample comprising the steps of:
   (a) providing a biological sample;
   (b) combining said sample with a solid phase material having immobilized thereon a binding member specific for IgM antibodies;
   (c) allowing IgM antibodies, if any, specific to said binding member immobilized on said solid phase material to bind to said immobilized binding member to form a binding member-IgM antibody complex;

(d) separating said solid phase material from said sample;

(e) washing said separated solid phase material with a sufficient amount of a rheumatoid factor neutralization buffer to dissociate said rheumatoid factors from IgG antibodies bound to said solid phase material;

(f) subjecting said solid phase material after step (e) to an antibody-enzyme conjugate that will bind to said binding member-IgM antibody complex, if any, to form an immunocomplex;

(g) removing unbound materials from said solid phase material subsequent to step (f);

(h) adding a substrate for said enzyme to said immunocomplex;

(i) measuring rate of formation of detectable product resulting from the reaction of said enzyme with said substrate.

19. The method of claim 18, further including the step of removing unbound materials from said washed, separated solid phase material subsequent to step (e).

20. The method of claim 18, wherein said binding member immobilized on said solid phase material is rubella virus antigen.

21. The method of claim 18, wherein said binding member immobilized on said solid phase material is a *Toxoplasmosis gondii* antigen.

22. The method of claim 18, wherein said solid phase material is a microparticle.

23. The method claim 18, wherein said enzyme is alkaline phosphatase.

24. The method of claim 18, wherein said substrate for said enzyme is 4-methylumbellifery phosphate.

25. A method for measuring the amount of IgM antibodies in an assay of a biological sample comprising the steps of:

(a) providing a biological sample;

(b) providing a reagent comprising a solid phase material having immobilized thereon a binding member specific for IgM antibodies;

(c) diluting said sample of step (a) or said reagent of step (b) or both said sample of step (a) and said reagent of step (b) with a sufficient amount of rheumatoid factor neutralization buffer to prevent rheumatoid factors from binding to IgG antibodies bound to said solid phase material;

(d) combining said biological sample of (a) and said reagent of (b) under conditions whereby IgM antibodies, if any, specific to said binding member, bind to said immobilized binding member to form a binding member-IgM antibody complex;

(e) separating said solid phase material from said sample;

(f) subjecting said solid phase material of step (e) to an antibody-enzyme conjugate that will bind to said binding member-IgM antibody complex, if any, to form an immunocomplex;

(g) removing unbound materials from said solid phase material subsequent to step (f);

(h) adding a substrate for said enzyme to said immunocomplex;

(i) measuring rate of formation of detectable product resulting from the reaction of said substrate with said enzyme.

26. The method of claim 25, further including the step of removing unbound materials from said solid phase material subsequent to step (e).

27. The method of claim 25, wherein said binding member immobilized on said solid phase material is rubella virus antigen.

28. The method of claim 25, wherein said binding member immobilized on said solid phase material is *Toxoplasmosis gondii* antigen.

29. The method of claim 25, wherein said solid phase material is a microparticle.

30. The method claim 25, wherein said enzyme is alkaline phosphatase.

31. The method of claim 25, wherein said substrate for said enzyme is 4-methylumbelliferyl phosphate.

* * * * *